(12) United States Patent
Loveless et al.

(10) Patent No.: US 10,766,834 B2
(45) Date of Patent: Sep. 8, 2020

(54) TRANSALKYLATION PROCESSES AND CATALYST COMPOSITIONS USED THEREIN

(71) Applicant: ExxonMobil Chemical Patents Inc., Baytown, TX (US)

(72) Inventors: Brett T. Loveless, Houston, TX (US); Daniel J. Benedict, Houston, TX (US); Kathleen M. Keville, Beaumont, TX (US); Juan D. Henao, Houston, TX (US); Matthew S. Ide, Doylestown, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 111 days.

(21) Appl. No.: 15/899,096

(22) Filed: Feb. 19, 2018

(65) Prior Publication Data
US 2018/0251413 A1    Sep. 6, 2018

Related U.S. Application Data

(60) Provisional application No. 62/467,415, filed on Mar. 6, 2017.

(51) Int. Cl.
| | | |
|---|---|---|
| *C07C 6/10* | (2006.01) | |
| *B01J 29/70* | (2006.01) | |
| *B01J 29/08* | (2006.01) | |
| *C07C 15/04* | (2006.01) | |
| *C07C 15/073* | (2006.01) | |
| *C07C 6/12* | (2006.01) | |
| *B01J 29/18* | (2006.01) | |

(52) U.S. Cl.
CPC .............. *C07C 6/10* (2013.01); *B01J 29/08* (2013.01); *B01J 29/18* (2013.01); *B01J 29/7007* (2013.01); *B01J 29/7038* (2013.01); *C07C 6/126* (2013.01); *C07C 15/04* (2013.01); *C07C 15/073* (2013.01); *C07C 2529/08* (2013.01); *C07C 2529/18* (2013.01); *C07C 2529/70* (2013.01); *C07C 2529/80* (2013.01); *Y02P 20/52* (2015.11)

(58) Field of Classification Search
CPC ........... C07C 6/10; C07C 6/126; C07C 15/04; C07C 15/073; C07C 2529/08; C07C 2529/18; C07C 2529/70; C07C 2529/80; B01J 29/08; B01J 29/18; B01J 29/7007; B01J 29/7038; Y02P 20/52
See application file for complete search history.

(56) References Cited

U.S. PATENT DOCUMENTS

| | | |
|---|---|---|
| 4,185,040 A | 1/1980 | Ward et al. |
| 4,992,606 A | 2/1991 | Kushnerick et al. |
| 5,073,653 A | 12/1991 | Butler |
| 5,600,050 A | 2/1997 | Huang et al. |
| 2008/0167508 A1* | 7/2008 | Clark ................... C07C 2/66 585/446 |

FOREIGN PATENT DOCUMENTS

| | | |
|---|---|---|
| GB | 1292228 A | 10/1972 |
| WO | 2010/042327 A | 4/2010 |
| WO | 2014182434 A | 11/2014 |

OTHER PUBLICATIONS

Perego, C. et al. "Recent advances in the industrial alkylation of aromatics: new catalysts and new processes" Catalysis Today, vol. 73 pp. Mar. 22, 2002.
IUPAC Periodic Table of the Elements, International Union of Pure and Applied Chemistry, May 1, 2013.

* cited by examiner

*Primary Examiner* — In Suk C Bullock
*Assistant Examiner* — Jason Y Chong
(74) *Attorney, Agent, or Firm* — Darryl M. Tyus

(57) ABSTRACT

Disclosed are selectivated transalkylation catalyst compositions and methods of making the same. The selectivated transalkylation catalyst compositions have a zeolite framework structure of MWW, FAU, BEA*, or MOR, or mixtures thereof, and are selectivated with a selectivating solution. The selectivating solution includes a dissolved ion of at least one element in Group 1, Group 2, Group 15, Group 16, or Group 17 of the Periodic Table. Also disclosed are processes of producing ethylbenzene and cumene using the selectivated transalkylation catalyst compositions.

14 Claims, 1 Drawing Sheet

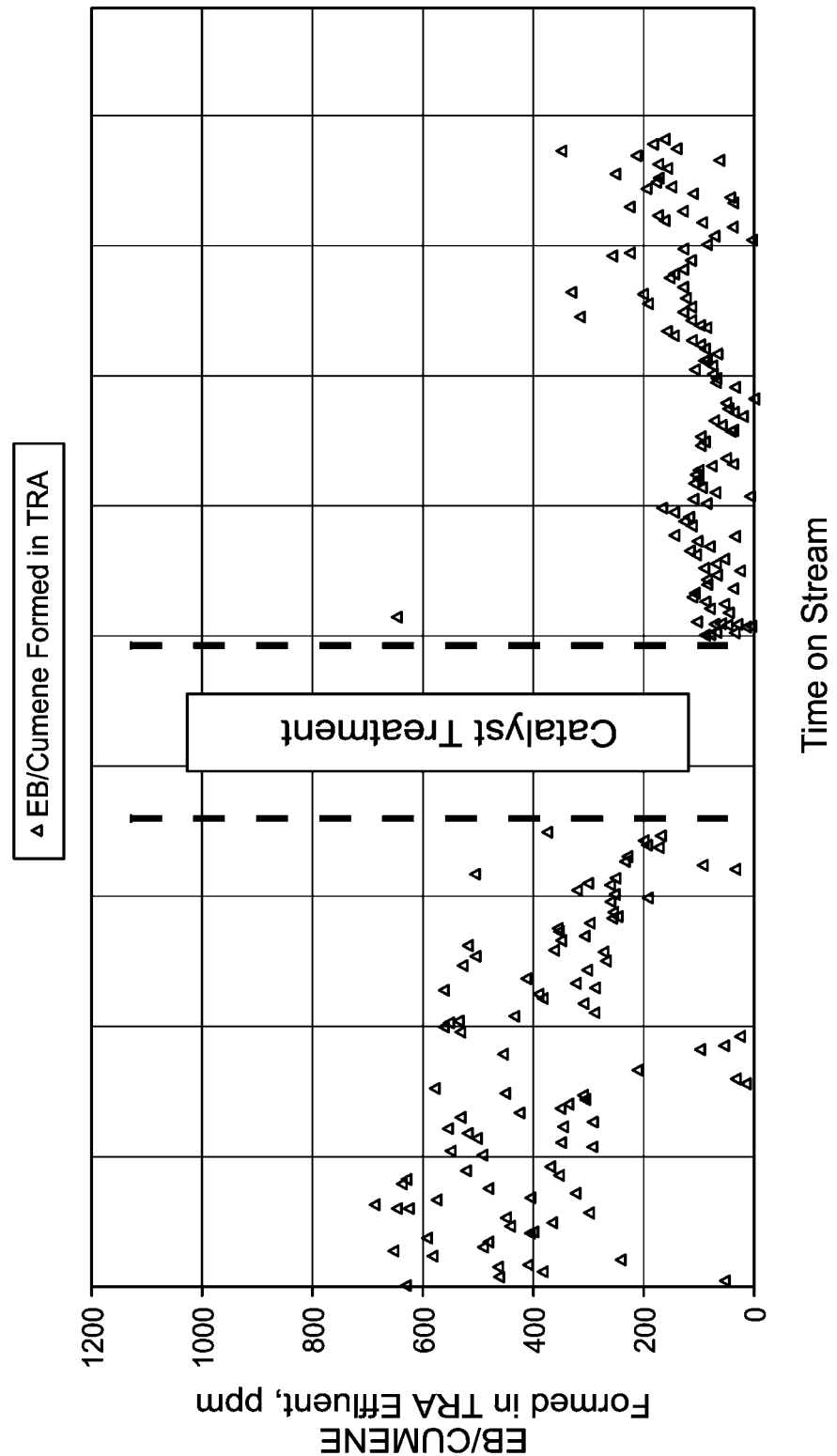

TRANSALKYLATION PROCESSES AND CATALYST COMPOSITIONS USED THEREIN

CROSS REFERENCE TO RELATED APPLICATION

This application claims priority to and the benefit of U.S. Provisional Application No. 62/467,415, filed Mar. 6, 2017, incorporated herein by reference in its entirety.

FIELD OF THE INVENTION

The present disclosure relates to transalkylation catalyst compositions useful in the production of ethylbenzene, cumene or other mono-alkylated aromatic compounds.

BACKGROUND OF THE INVENTION

Historically, the commercial production of ethylbenzene was dominated by liquid-phase aluminum chloride catalyzed processes until the early 1980s when the first vapor-phase zeolite-based process was introduced. The zeolite vapor-phase technology subsequently achieved commercial success because it proved to be more efficient and avoided the difficulty of handling aluminum chloride. However, vapor-phase processes operate at high temperatures and produce considerable by-products. While improvements were made over the years, it was not until the arrival of liquid-phase processing in the early 1990s that zeolite-based technologies could produce a high-purity ethylbenzene product.

More specifically, to produce ethylbenzene, polymer grade ethylene can be reacted with benzene that is in stoichiometric excess under liquid-phase conditions in a fixed-bed, multi-stage alkylation reactor. Ethylene conversion is essentially complete, with selectivity to ethylbenzene in the alkylation reaction at over 90%. Unreacted benzene is then separated and recycled back to the reaction section. Ethylbenzene product is recovered from polyethylbenzenes. Polyethylbenzene is then fed to a fixed-bed transalkylation reactor and converted into additional ethylbenzene product by reacting with excess benzene. The molar yield of ethylbenzene for the overall process can exceed 99.5% relative to both ethylene and benzene. However, the non-molar yield of 0.5 percent can include trace compounds such as sodium, calcium, potassium, chlorine, iron, titanium, sulfur and zinc that can result in undesired byproducts.

Cumene is an important intermediate in the chemical and polymer industries, with global cumene production currently exceeding twelve million metric tons annually. Cumene is generally produced by the alkylation of benzene with a $C_3$ alkylating age (e.g., propylene) in the presence of an acid catalyst. Early cumene plants used solid phosphoric acid as the catalyst, but more recently most cumene manufacturers have replaced the phosphoric acid with molecular sieve catalysts. Examples of benzene alkylation processes employing molecular sieve catalysts can be found in, for example, U.S. Pat. Nos. 4,185,040; 4,992,606; and 5,073,653.

Processes for production of cumene using molecular sieve or zeolite-based catalysts can be conducted in either the vapor phase or the liquid phase. However, in view of the improved selectivity and decreased capital and operating costs associated with liquid phase operation, many commercial cumene processes now operate under at least partially liquid phase conditions.

The selectivity to the desirable ethylbenzene and cumene is important to the economics of the catalytic transformation of both feed stock and recycle streams for zeolite-based catalysts used in liquid phase alkylation and transalkylation systems. Improvements in selectivity can advance raw material utilization and debottleneck existing processes. For example, ethylbenzene can be produced in very high molar yields under liquid-phase conditions in fixed bed, multi-stage alkylation reactor using zeolite-based catalysts. Yet, certain "non-selective" catalytic sites exist on otherwise "selective" catalyst and result in increased yields of undesirable byproduct during reaction and reduce the selectivity to the desirable products.

A need exists, therefore, for methods that suppress "non-selective" catalyst sites on transalkylation catalysts and cause the non-selective sites on the surface, or within the interior channels, of the catalysts to become inactive so to avoid the production of undesired byproducts and improve selectively of products to be produced.

SUMMARY OF THE INVENTION

Selectivated transalkylation catalyst compositions and process for producing ethylbenzene or cumene using such compositions are provided herein. These selectivated transalkylation catalysts produce a lower ratio of undesirable/desirable compounds, such as the ethylbenzene/cumene or xylenes/ethylbenzene, than the transalkylation catalyst composition (which has not been contacted with a selectivating solution) in a transalkylation effluent stream when the catalysts are compared under equivalent transalkylation conditions. More specifically, the ratio of ethylbenzene to cumene in the alkylation effluent stream after treatment with the selectivated transalkylation catalyst composition can be as low as 500 ppm, 400 ppm or 375 ppm.

In a first aspect, the selectivated transalkylation catalyst composition and the transalkylation catalyst composition each comprise a zeolite having a framework structure selected from the group consisting of FAU, BEA*, MOR, MWW and mixtures thereof. The FAU framework structure is selected from the group consisting of 13X, low sodium ultrastable Y (USY), dealuminized Y (Deal Y), ultrahydrophobic Y (UHP-Y), rare earth exchanged Y (REY), rare earth exchanged USY (RE-USY), and mixtures thereof. The zeolite having BEA* framework structure is zeolite beta. The zeolite having the MOR framework structure is selected from the group consisting of mordenite, EMM-34, TEA-mordenite, and mixtures thereof. The zeolite having the MWW framework structure is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, UZM-37, MIT-1, ITQ-1, ITQ-2, ITQ-30 and mixtures of two or more thereof. Furthermore, the zeolite comprises from 65 wt. % to 80 wt. % of the selectivated transalkylation catalyst composition and/or transalkylation catalyst composition.

In a second aspect, the selectivated transalkylation catalyst composition of this invention is formed by contacting an untreated transalkylation catalyst composition with a selectivating solution. The selectivating solution comprises water and a dissolved ion. The ion is selected from an element in Group 1, Group 2, Group 15, Group 16, or Group 17 of the Periodic Table to form a selectivated transalkylation catalyst. In an aspect, the element in Group 1, Group 2, Group 15, Group 16, or Group 17 of the Periodic Table is a cation or an anion dissolved in the selectivating solution. More specifically, the element in Group 1 is sodium or potassium, the element in Group 2 is calcium, the element in Group 15 is phosphorus, the element in Group 16 is sulfur, and the element in Group 17 is chlorine.

Advantageously, the untreated transalkylation catalyst composition is contacted with the selectivating solution for 1 hour or more at a temperature in the range of 20° C. to 95° C. In addition, the untreated or selectivated transalkylation catalyst composition can be further contacted with benzene for 24 hours or more. Also, the selectivated transalkylation catalyst composition can be dried with an inert gas, preferably comprising nitrogen, air or a mixture thereof, for 1 hour or more at ambient pressure and at temperature of less than 300° C.

In a third aspect, processes for producing ethylbenzene or cumene are further provided. These processes include a transalkylation reaction using any one of the selectivated transalkylation catalyst composition of this invention, an alkylation reaction and the pretreatment of the aromatic and non-aromatic feeds streams using a guard bed material to produce mono-alkylated aromatic compounds, such as, for example, ethylbenzene and cumene. The transalkylation reaction of the processes include the following steps. Step (a) of providing any one of the selectivated transalkylation catalyst compositions of this invention to a transalkylation reaction zone. The selectivated transalkylation catalyst composition is made by contacting the transalkylation catalyst composition with a selectivating solution, as described herein. Step (b) of providing a stream comprising a poly-alkylated aromatic compound, such as di-ethylbenzene or di-isopropyl benzene, and a stream comprising an alkylatable aromatic compound, such as benzene, to the transalkylation reaction zone. Step (c) of contacting the poly-alkylated aromatic compound stream with the alkylatable aromatic compound stream in the presence of the selectivated transalkylation catalyst composition under at least partially liquid phase transalkylation conditions to produce a transalkylation effluent stream of ethylbenzene or cumene. The present processes may also include a step of separating the transalkylation effluent stream to recover an ethylbenzene stream or a cumene stream.

Advantageously, the present processes can include a step of contacting a benzene stream with an alkylating agent stream under alkylation conditions and in the presence of an alkylation catalyst to produce an alkylation effluent which comprises mono-alkylated benzene, such as ethylbenzene or cumene, and poly-alkylated benzene. The alkylating agent stream can include ethylene, propylene or a mixture thereof. The alkylation conditions can be at least partially liquid phase conditions. The alkylation effluent, which can include ethylbenzene ("EB") and isopropyl benzene ("cumene"), may be separated to recover the by-product poly-alkylated benzene stream which is supplied to the transalkylation reaction.

BRIEF DESCRIPTION OF THE DRAWING

The FIGURE is a graph depicting the ratio of EB/cumene in transalkylation effluent as used as a measure of transalkylation selectivity of the transalkylation catalyst composition to cumene.

DESCRIPTION OF THE PREFERRED EMBODIMENTS

Provided herein are selectivated transalkylation catalyst compositions which can produce a lower amount of the ethylbenzene by-product in a cumene process or a lower amount of xylene by-product of an ethylbenzene process. That is, a lower ratio of ethylbenzene/cumene or xylenes/ethylbenzene in a transalkylation effluent stream than the transalkylation catalyst composition when compared under equivalent transalkylation conditions. More specifically, the ratio of ethylbenzene to cumene in the alkylation effluent stream after treatment with the selectivated transalkylation catalyst composition can be as low as 500 ppm, 400 ppm or 375 ppm.

Zeolites are microporous aluminosilicates that can be used as solid Brønsted acid catalysts with wide application in both the refining and petrochemical industries. The unique structure of certain zeolites, such as the 12-membered ring surface pockets of the MWW framework, can enable "shape-selective" chemical transformations that offer significant benefits to other "non-selective" catalysts. Dissolved ions in the feed and recycle streams can prevent or reverse the hydrolysis reaction of the strong Lewis acid sites which cause the Lewis acid sites (proton acceptor) to become Brønsted acid (proton donor) sites. Yet, as described herein, certain "non-selective" catalytic sites can exist on an otherwise "selective" catalyst, resulting in increased yields of undesired byproducts during a chemical transformation. We have discovered that metal cations will suppress "non-selective" catalyst sites on the transalkylation catalyst composition and improve transalkylation selectivity as measured by the ratio of ethylbenzene to cumene in a transalkylator effluent.

Definitions

The terms "a" and "the" as used herein are understood to encompass the plural as well as the singular.

The term "alkylatable aromatic compound" as used herein means an aromatic compound that may receive an alkyl group. One non-limiting example of an alkylatable aromatic compound is benzene The term "alkylating agent" as used herein means a compound which may donate an alkyl group to an alkylatable aromatic compound. Non-limiting examples of an alkylating agent are ethylene, propylene, and butylene. Another non-limiting example is any poly-alkylated aromatic compound that is capable of donating an alkyl group to an alkylatable aromatic compound.

The term "catalyst poison" as used herein means one or more impurities, as defined herein, which acts to reduce the cycle length of a molecular sieve or a catalyst.

The term "comprising" (and its grammatical variations) as used herein is used in the inclusive sense of "having" or "including" and not in the exclusive sense of "consisting only of."

The term "Constraint Index" as used herein is a convenient measure of the extent to which an aluminosilicate or molecular sieve provides controlled access to molecules of varying sizes to its internal structure. For example, aluminosilicates or molecular sieves which provide a highly-restricted access to and egress from its internal structure have a high value for the Constraint Index, and aluminosilicates or molecular sieves of this kind usually have pores of small size, e.g. less than 5 Angstroms. On the other hand, aluminosilicates or molecular sieves which provide relatively free access to the internal aluminosilicate structure have a low value for the constraint index, and usually pores of large size. The method by which Constraint Index may be determined is described fully in U.S. Pat. No. 4,016,218, incorporated herein by reference.

The term "cycle length" as used herein means the total on-oil time between regenerations, or the on-oil time period between fresh load and regeneration. After the fresh catalyst or regenerated catalyst composition being brought on-oil, the catalyst composition may be deactivated due to coke deposition or adsorption of catalyst poisons. As the catalyst composition becomes deactivated, the reaction zone has to be operated at higher temperatures to maintain the same productivity or catalytic activity. The catalyst composition has to be regenerated once the reaction zone temperature reaches a threshold temperature, typically determined by metallurgy of the reactor or when economic factors warrant.

The term "at least partially liquid phase" as used herein, means a mixture having at least 1 wt. % liquid phase, optionally at least 5 wt. % liquid phase, at a given temperature, pressure, and composition.

The term "at least partially deactivated", or "deactivated", when used in connection with the transalkylation catalyst composition herein means that the catalytic activity of such material or catalyst has decreased by an amount of at least 1% as compared to initial catalytic activity of the fresh transalkylation catalyst composition.

The term "framework type" as used herein has the meaning described in the "Atlas of Zeolite Framework Types," by Ch. Baerlocher, W. M. Meier and D. H. Olson (Elsevier, 5th Ed., 2001).

The term "fresh" when used in connection with the transalkylation catalyst composition herein means the molecular sieve or such catalyst has not been used in a catalytic reaction after being manufactured.

The term "impurities" as used herein includes, but is not limited to, compounds having at least one of the following elements: nitrogen, halogens, oxygen, sulfur, arsenic, selenium, tellurium, phosphorus, and Group 1 through Group 12 metals of the Periodic Table. Such impurities, includes, but is not in any way limited to, organic nitrogenous impurities.

The term "MCM-22 family material" (or "MCM-22 family molecular sieve"), as used herein, can include: (i) molecular sieves made from a common first degree crystalline building block "unit cell having the MWW framework topology." A unit cell is a spatial arrangement of atoms which is tiled in three-dimensional space to describe the crystal as described in the "Atlas of Zeolite Framework Types," by Ch. Baerlocher, W. M. Meier and D. H. Olson (Elsevier, 5th Ed., 2001); (ii) molecular sieves made from a common second degree building block, a 2-dimensional tiling of such MWW framework type unit cells, forming a "monolayer of one unit cell thickness," preferably one c-unit cell thickness; (iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, and any combination thereof; or (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Members of the MCM-22 family include, but are not limited to, MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent 0293032), ITQ-1 (described in U.S. Pat. No. 6,077,498), ITQ-2 (described in International Patent Publication No. WO97/17290), ITQ-30 (described in International Patent Publication No. WO20051 18476), MCM-36 (described in U.S. Pat. No. 5,250,277), MCM-49 (described in U.S. Pat. No. 5,236,575), MCM-56 (described in U.S. Pat. No. 5,362,697); and an EMM-10 family molecular sieve (described or characterized in U.S. Pat. Nos. 7,959,899 and 8,110, 176; and U.S. Patent Application Publication No. 2008/0045768), such as EMM-10, EMM-10-P, EMM-12 and EMM-13.

The term "mono-alkylated aromatic compound" means an aromatic compound that has only one alkyl substituent. Non-limiting examples of mono-alkylated aromatic compounds are ethylbenzene, isopropyl benzene (cumene) and sec-butylbenzene.

As used herein, the term "Periodic Table" means the Periodic Table of the Elements of the International Union of Pure and Applied Chemistry (IUPAC), dated 1 May 2013, as it appears on the inside cover of The Merck Index, Twelfth Edition, Merck & Co., Inc., 1996.

The term "poly-alkylated aromatic compound" as used herein means an aromatic compound that has more than one alkyl substituent. A non-limiting example of a poly-alkylated aromatic compound is poly-alkylated benzene, e.g., di-ethylbenzene, tri-ethylbenzene, di-isopropyl benzene, and tri-isopropyl benzene.

The molecular sieve having a FAU framework structure type is selected from the group consisting of zeolite Y, low sodium ultrastable Y (USY), dealuminized Y (Deal Y), ultra hydrophobic Y (UHP-Y), rare earth exchanged Y (REY), rare earth exchanged USY (RE-USY), zeolite X, and mixtures thereof. The molecular sieve having a *BEA framework structure type is zeolite beta. The molecular sieve having a MWW framework structure type is a MCM-22 family material, as defined herein. The MCM-22 family material includes one or more of ERB-1, ITQ-1, ITQ-2, ITQ-30, PSH-3, SSZ-25, MCM-22, MCM-36, MCM-49, MCM-56, EMM-10, EMM-10P, EMM-12, EMM-13 and mixtures thereof. The molecular sieve having a MOR framework structure type is selected from the group consisting of mordenite, TEA-mordenite and mixtures thereof.

Related zeolites to be included in the MCM-22 family are UZM-8 (described in U.S. Pat. No. 6,756,030), UZM-8HS (described in U.S. Pat. No. 7,713,513), UZM-37 (described in U.S. Pat. No. 8,158,105), MIT-1 is described in Chem. Sci., 2015, 6, 6320-6324, all of which are also suitable for use as the molecular sieve of the MCM-22 family.

Zeolite ZSM-3 is described in U.S. Pat. No. 3,415,736. Zeolite ZSM-18 is described in U.S. Pat. No. 3,950,496. Linde Type X is described in French Patent No. 1,117,756. Linde Type A is described in French Patent No. 1,117,776. Zeolite ZSM-14 is described in U.S. Pat. No. 3,923,636. Zeolite ZSM-20 is described in U.S. Pat. No. 3,972,983. Zeolite beta is described in U.S. Pat. No. 3,308,069, and U.S. Reissue Pat. No. 28,341. Low sodium ultrastable Y molecular sieve (USY) and rare earth exchanged USY (RE-USY) are described in U.S. Pat. Nos. 3,293,192 and 3,449,070. Dealuminized Y zeolite (Deal Y) may be prepared by the method found in U.S. Pat. No. 3,442,795. Ultra hydrophobic Y (UHP-Y) is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

Transalkylation Catalyst Composition and its Method of Making

As described herein, both transalkylation catalyst compositions and selectivated transalkylation catalyst compositions comprise a zeolite in acid form and having a framework structure selected from the group consisting of FAU, BEA*, MOR, MWW and mixtures thereof and are useful in alkylation processes for production of ethylene and cumene. The transalkylation catalyst composition has one or more non-selective catalyst sites which are deactivated by the dissolved ions in the selectivating solution. Each selectivated transalkylation catalyst composition comprises a plurality of unreactive complexes formed within one or more or a plurality of unselective catalyst sites present within the transalkylation catalyst composition.

The FAU framework structure can be selected from the group consisting of 13X, low sodium ultrastable Y (USY), dealuminized Y (Deal Y), ultrahydrophobic Y (UHP-Y), rare earth exchanged Y (REY), rare earth exchanged USY (RE-USY), and mixtures thereof. The zeolite having BEA* framework structure is zeolite beta. The zeolite having the MOR framework structure can be selected from the group consisting of mordenite, EMM-34, TEA-mordenite, and mixtures thereof. The zeolite having the MWW framework structure can be selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, UZM-37, MIT-1, ITQ-1, ITQ-2, ITQ-30 and mixtures of two or more thereof. Furthermore, the amount of zeolite in the transalkylation catalyst composition can be between 1 wt. % to 100 wt. %, preferably from 65 wt. % to 80 wt. % of the transalkylation catalyst composition.

The transalkylation catalyst composition can include a fresh alkylation or transalkylation catalyst, an at least partially deactivated alkylation or transalkylation catalyst, or combinations thereof. In an aspect, partially deactivated transalkylation catalyst are deactivated by coke deposition during its prior use in an alkylation or transalkylation process.

The zeolite can be combined in a conventional manner with an oxide binder, such as alumina, to form the final transalkylation or alkylation catalyst compositions. The transalkylation or alkylation catalyst compositions can be a fresh catalyst composition, for example, made as described herein, or an at least partially deactivated catalyst composition, for example, deactivated in a previous alkylation reaction, or can be a regenerated catalyst composition using any known methods in the art. The transalkylation or alkylation catalyst compositions can be calcined at a temperature of greater than about 300° C. by any known method.

In an aspect, the transalkylation catalyst composition can be contacted with the selectivating solution. The selectivating solution comprises water and a cation or an anion of an element in Group 1, Group 2, Group 15, Group 16, or Group 17 of the Periodic Table, in which such cation or anion is dissolved in the selectivation solution. The element in Group 1 is preferably sodium or potassium. The element in Group 2 is preferably calcium. The element in Group 15 is preferably phosphorus. The element in Group 16 is preferably sulfur. The element in Group 17 is preferably chlorine.

In one or more embodiments, the selectivating solution comprises dissolved ions which include one or more of the following elements: calcium in an amount from 600 to 750 milligrams per liter (mg/L), sodium in an amount from 400 to 500 mg/L, potassium in an amount from 40 to 80 mg/L, chlorine in an amount from 650 to 850 mg/L, and sulfur in an amount of 750 to 950 mg/L. In one or more embodiments, the pH of the selectivating solution is in the range of 6.5 to 8.0.

The selectivating solution is contacted with the catalyst composition for one hour or more, at a temperature above 0° C., or in the range of 20° C. to 95° C., or in the range of 25° C. to 90° C.

After contacting with the selectivating solution, the selectivated catalyst composition is then dried at a temperature of less than about 300° C.; for example, from about 50° C. to about 250° C., or less than about 200° C.; for example, from about 50° C. to about 180° C., or from about 100° C. to about 160° C., or from about 120° C. to about 150° C., or less than 150° C.; for example, from about in 80° C. to 100° C., or 50° C. to less than 150° C., or from about 120° C. to less than about 150° C.

Drying of the catalyst composition can be conducted with an inert gas, preferably a flowing inert drying gas. The drying gas can flow at any direction. The drying gas can be any gas that is not reactive under the drying conditions (e.g., inert gas), such as air, nitrogen, oxygen, or any other suitable gas. The inert gas may comprise nitrogen, oxygen, air or a mixture thereof. The temperature of drying gas can be less than 300° C., less than about 200° C.; for example, from about 50° C. to about 180° C., or from about 100° C. to about 160° C., or from about 120° C. to about 150° C. The dryer can be a fixed or moving shallow dryer.

In one or more embodiments, the selectivated catalyst composition is contacted with an aromatic solvent, such as for example benzene, for 1 hour or more, 12 hours or more, or 24 hours or more, to remove any residual water for moisture.

The drying can be conducted for a period of greater than about 1 minute; for example, from 1 minute to about 96 hours, or about 30 minutes to 48 hours, or about 1 hour to 36 hours, or about 2 hours to about 24 hours in yet another aspect. As the transalkylation process proceeds, the transalkylation catalyst composition will gradually lose its alkylation activity, such that the reaction temperature required achieves a given performance parameter; for example, conversion of the alkylating agent will increase. When catalyst activity has decreased by some predetermined amount, typically 5% to 90% and, more preferably 10% to 50%, compared to the initial catalyst activity, the deactivated catalyst can be subjected to the treatment process described herein. For example, in some aspects, the deactivated catalyst can be regenerated using any known method and then treated with the selectivating solution.

Transalkylation and Alkylation Processes

The process described herein includes a transalkylation reaction using any one of the transalkylation catalyst composition of this invention, an alkylation reaction and the pretreatment of the aromatic and non-aromatic feeds streams using a guard bed material to produce mono-alkylated aromatic compounds, such as, for example, ethylbenzene and cumene. The transalkylation reaction of the processes includes the following steps. Step (a) of providing any one of the selectivated transalkylation catalyst compositions of this invention to a transalkylation reaction zone. Step (b) of providing a stream comprising a poly-alkylated aromatic compound, such di-ethyl benzene, and a stream comprising an alkylatable aromatic compound, such as a benzene, preferably, to a reaction zone. Step (c) of contacting the poly-alkylated aromatic compound stream with the alkylatable aromatic compound stream in the presence of the selectivated transalkylation catalyst composition under at least partially liquid phase transalkylation conditions to produce a transalkylation effluent stream which comprises the mono-alkylated aromatic stream, such as an ethylbenzene stream or a cumene stream. The processes can also include a step of separating the transalkylation effluent stream to recover an ethylbenzene stream or a cumene stream.

The selectivated transalkylation catalyst composition produces a lower ratio of ethylbenzene/cumene or xylenes/ethylbenzene than said transalkylation catalyst composition that has not been contacted with a selectivating solution when the catalysts are compared under equivalent transalkylation conditions.

Also, the selectivated transalkylation catalyst composition has a higher selectivity to ethylbenzene or cumene than the selectivity of transalkylation catalyst composition that has not been contacted with the selectivating solution when compared under equivalent transalkylation conditions.

The alkylation step of the process comprises step (e) of contacting a benzene stream with an alkylating agent stream under alkylation conditions and in the presence of an alkylation catalyst to produce an alkylation effluent which comprises mono-alkylated benzene and said poly-alkylated benzene.

Poly-alkylated aromatic compounds are normally produced as a by-product of an alkylation step in which a benzene stream is contacted with an alkylating agent stream under suitable alkylation conditions and in the presence of an alkylation catalyst to produce an alkylation effluent which comprises mono-alkylated benzene as well as said poly-alkylated benzene. Such suitable alkylation condition are at least partially liquid phase conditions The alkylation effluent stream is separated to recover a mono-alkylated aromatic compound stream and a poly-alkylated aromatic compound stream that may be supplied to the transalkylation reaction, preferably to step (b).

The feeds to the process may contain catalyst poisons which deactivate the alkylation and transalkylation catalyst compositions. To solve this problem, a by-passable reactive or unreactive guard bed may normally be utilized. Such guard bed is loaded with a guard bed material and may be located in the first bed of the alkylation reactor, in addition to, and upstream of, the reaction zones used for alkylation or transalkylation. The guard bed material may be the same or different from the catalyst used in the alkylation or transalkylation reaction zone(s). Such guard bed is maintained from under ambient conditions, such as in a non-reactive guard bed, or at suitable alkylation or transalkylation conditions, such as in a reactive guard bed. The feeds to the guard beds include at least a portion of alkylatable aromatic compound, and optionally at least a portion of the alkylating agent. These feeds are contacted with the guard bed material in a non-reactive guard bed or a reactive guard bed. The non-reactive guard bed is an absorptive zone where the catalyst poisons in the feeds, which could otherwise poison the alkylation or transalkylation catalyst and reduce their cycle length, are absorbed by the guard bed material. There is no alkylating agent in the non-reactive guard bed. However, in the reactive guard bed the alkylating agent is present to affect the desired alkylation reaction, but also it serves to remove any catalyst poisons by absorption.

In the reactive or non-reactive guard bed, at least a portion of the stream comprising the alkylatable aromatic compound, such as benzene, is contacted with a guard bed material under suitable non-reactive guard bed conditions to remove at least a portion of the catalyst poisons to produce a treated stream. In the reactive guard bed, at least a portion of the alkylating agent is also contacted with the guard bed material under suitable reactive guard bed conditions to alkylate the alkylatable aromatic compound to form an alkylated aromatic compound.

The guard bed material in the reactive or unreactive guard bed is therefore subject to more frequent regeneration and/or replacement than the remainder of the alkylation or transalkylation catalyst, and hence the guard bed is typically provided with a by-pass circuit so that the alkylation feed(s) may be fed directly to the series connected reaction zones in the reactor while the guard bed is out of service. The reactive or unreactive guard bed may be operated in co-current upflow or downflow operation. One example of an aromatics alkylation system including a reactive guard bed is disclosed in U.S. Pat. No. 6,995,295, the entire contents of which are incorporated herein by reference.

The guard bed material comprises a molecular sieve, and in an aspect, the molecular sieve that may be used is a large pore zeolite having a Constraint Index of less than 2. Such large pore zeolites include, but are not limited to, for example, a molecular sieve having a framework structure type selected from the group consisting of FAU, *BEA, MWW, MOR and mixtures thereof. Other suitable large pore zeolites that may be used include, but are not limited to, ZSM-3, ZSM-4, ZSM-14, ZSM-18, and ZSM-20, as well as Linde Type X, Linde type A and mixtures thereof.

In one or more embodiments, the stream comprising benzene further comprises impurities, said stream is contacted with a guard bed material to remove at least a portion of said impurities, said guard bed material comprises a large pore zeolite having a framework structure type selected from the group consisting of FAU, *BEA, MWW, MOR and mixtures thereof.

Alkylatable Aromatic Compounds

Substituted alkylatable aromatic compounds which can be alkylated herein have at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable alkylatable aromatic hydrocarbons include benzene, naphthalene, anthracene, naphthacene, perylene, coronene, and phenanthrene.

Generally, the alkyl groups, which can be present as substituents on the aromatic compound, contain from 1 to about 22 carbon atoms and usually from about 1 to 8 carbon atoms, and most usually from about 1 to 4 carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalene; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Often an alkylate is obtained as a high boiling fraction in which the alkyl group attached to the aromatic nucleus varies in size from about Ce to about $C_{12}$. When cumene or ethylbenzene is the desired product, the present processes produce little byproducts such as xylenes. The xylenes made in such instances may be less than about 500 ppm.

In addition, reformate containing substantial quantities of benzene, toluene and/or xylene are useful as a feed/feed stock for the processes described herein.

Alkylating Agents

The alkylating agents useful in the processes described herein include any aliphatic or aromatic organic compound having one or more available alkylating olefinic groups capable of reaction with the alkylatable aromatic compound, such as an alkylating group possessing from 1 to 5 carbon atoms, or poly-alkylated aromatics compound(s). Examples of suitable alkylating agents include olefins such as ethylene, propylene, the butenes, and the pentenes; alcohols (inclusive of monoalcohols, dialcohols, trialcohols, etc.), such as methanol, ethanol, the propanols, the butanols, and the pentanols; aldehydes such as formaldehyde, acetaldehyde, propionaldehyde, butylraldehyde, and n-valeraldehyde; and alkyl halides such as methyl chloride, ethyl chloride, the propyl chlorides, the butyl chlorides, and the pentyl chlorides, and so forth.

Mixtures of light olefins are especially useful as alkylating agents in the alkylation process. Accordingly, mixtures of ethylene, propylene, butenes, and/or pentenes which are primary constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein.

Poly-alkylated aromatic compounds produced by the processing described herein include ethylbenzene, polyethylbenzene such as di-ethylbenzene, polyisopropylbenzene (cumene) such as di-isopropylbenzene, and/or mixtures thereof.

For example, a typical FCC light olefin stream possesses the following composition as shown in Table I:

TABLE I

|  | Wt. % | Mol. % |
| --- | --- | --- |
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-butane | 3.3 | 2.6 |
| Butenes | 22.1 | 18.32 |
| Pentanes | 0.7 | 0.4 |

More specifically, reaction products produced from the processes described herein include ethylbenzene from the reaction of benzene with ethylene, cumene from the reaction of benzene with propylene, ethyl toluene from the reaction of toluene with ethylene, cymenes from the reaction of toluene with propylene, and sec-butylbenzene from the reaction of benzene and n-butenes.

The reactants are in at least partially liquid phase and can be neat, i.e., free from intentional admixture or dilution with other material, or brought into contact with a zeolite catalyst composition with the aid of carrier gases or diluents such as, for example, hydrogen or nitrogen.

Alkylation and/or Transalkylation Conditions

A transalkylation reaction can be conducted in the at least partially liquid phase under suitable conditions such that the poly-alkylated aromatics react with the additional aromatic feed to produce additional mono-alkylated product. In an aspect, and as described herein, such transalkylation conditions can include at least one of the following: a temperature of about 100° C. to about 300° C., or from about 100° C. to about 275° C., a pressure of about 200 kPa to about 600 kPa, or about 200 kPa to about 500 kPa, a weight hourly space velocity (WHSV) based on the total feed of about 0.5 $hr^{-1}$ to about 100 $hr^{-1}$ on total feed, and aromatic/poly-alkylated aromatic compound weight ratio 1:1 to 6:1.

The alkylation processes and/or transalkylation processes described herein are conducted such that the organic reactants, i.e., the alkylatable aromatic compound and the alkylating agent, can be brought into contact with an alkylation or transalkylation catalyst in a suitable alkylation or transalkylation reaction zone, including, for example, a flow reactor containing a fixed bed of the catalyst composition, under effective and suitable alkylation and/or transalkylation conditions.

More specifically, alkylation conditions can include at least one of the following temperatures: about 10° C. to about 400° C.; about 50° C. to about 400° C.; or about 10° C. to about 200° C.; or about 70° C. to about 300° C.; or about 150° C. to about 300° C. Furthermore, alkylation conditions can include at least one of the following pressures: up to about 25000 kPa; or up to about 20000 kPa; from about 100 kPa to about 7000 kPa; from about 300 kPa to about 5000 kPa; or from about 689 kPa to about 4601 kPa. In addition, alkylation conditions can include at least one of the following molar ratios of alkylatable aromatic compound to alkylating agent: from about 0.1:1 to about 50:1, or about 0.5:1 to 10:1. Finally, alkylation conditions can include at least one of the following feed weight hourly space velocity (WHSV): between about 0.1 and about 100 $hr^{-1}$; from about 0.5 to 50 $hr^{-1}$; or from about 10 $hr^{-1}$ to about 100 $hr^{-1}$.

When benzene is alkylated with ethylene to produce ethylbenzene, the alkylation reaction may be carried out under at least partially liquid phase conditions as follows: at a temperature between about 150° C. and 300° C., or between about 200° C. and 260° C.; a pressure up to about 20000 kPa, or from about 200 kPa to about 5600 kPa; a WHSV of from about 0.1 $hr^{-1}$ to about 50 $hr^{-1}$, or from about 1 $hr^{-1}$ and about 10 $hr^{-1}$ based on the ethylene feed; and a ratio of the benzene to the ethylene in the alkylation reactor from 1:1 to 30:1 molar, preferably from about 1:1 to 10:1 molar.

When benzene is alkylated with propylene to produce cumene, the reaction may be carried out under at least partially liquid phase conditions as follows: a temperature of up to about 250° C., or from about 10° C. to about 200° C.; a pressure up to about 25000 kPa, or from about 100 kPa to about 3000 kPa; and a WHSV of from about 1 $hr^{-1}$ to about 250 $hr^{-1}$, or from 5 $hr^{-1}$ to 50 $hr^{-1}$, or from about 5 $hr^{-1}$ to about 10 $hr^{-1}$ based on the ethylene feed.

When the poly-alkylated aromatic compounds are polyethylbenzenes and are reacted with benzene to produce ethylbenzene, the transalkylation conditions include a temperature of from about 220° C. to about 260° C., a pressure of from about 300 kPa to about 400 kPa, weight hourly space velocity of 2 to 6 on total feed and benzene/PEB weight ratio 2:1 to 6:1.

When the poly-alkylated aromatic compounds are poly-isopropylbenzenes (PIPBs) and are reacted with benzene to produce cumene, the transalkylation conditions include a temperature of from about 100° C. to about 200° C., a pressure of from about 300 kPa to about 400 kPa, a weight hourly space velocity of 1 to 10 on total feed and benzene/PIPB weight ratio 1:1 to 6:1.

Selectivated transalkylation catalyst compositions and process for producing ethylbenzene or cumene using such compositions is more particularly described in the Example that follows.

EXAMPLES

The invention will now be more particularly described with reference to the following Example. Numerous modifications and variations are possible and it is to be understood that within the scope of the appended claims, the invention may be practiced otherwise than as specifically described herein.

Example

A transalkylation catalyst composition comprising 80 wt. % MCM-22 zeolite and 20 wt. % $Al_2O_3$ was contacted with liquid benzene in a fixed-bed, followed by benzene circulation and evacuation of the liquid benzene. The catalyst bed was then contacted by liquid water containing Group 1 and Group 2 cations of the Periodic Table, as well as dissolved chloride species, for about 26 hours at temperatures between 50-75° C. The water was subsequently drained from the fixed bed; the resulting catalyst material was then contacted with flowing nitrogen for about 10 days at ambient pressure and 80-100° C. The catalyst bed was then re-introduced to liquid benzene and contacted by a circulating stream of liquid benzene for about 3 days at 175° C. to remove any remaining water in the system. A stream of di-isopropyl benzene was then added to the benzene feed to the reactor, and the treated catalyst (i.e., a selectivated transalkylation catalyst composition) was put back into "transalkylation" service. The FIGURE shows the ratio of ethylbenzene (EB) to cumene (isopropyl benzene) formation, in ppm by weight, as a function of time in the transalkylation reactor effluent. Both time periods before and after the catalyst was contacted with the aqueous ion-containing stream (selectivating solution) are shown. EB is produced in the alkylator and transalkylator as a by-product of the cumene process. The amount of EB produced in the transalkylator is reduced when the selectivated transalkylation catalyst composition is returned to cumene service as indicated by the reduced EB/Cumene weight ratio as shown in the FIGURE.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

We claim:

1. A process for producing ethylbenzene comprising:
   (a) providing a selectivated transalkylation catalyst composition;
   (b) providing a stream comprising poly-alkylated benzene and a stream comprising benzene, wherein said stream comprising poly-alkylated benzene comprises di-ethylbenzene; and
   (c) contacting said stream comprising poly-alkylated benzene with said stream comprising benzene in presence of the selectivated transalkylation catalyst composition under at leas partially liquid phase transalkylation conditions to produce a transalkylation effluen stream comprising said ethylbenzene,
   wherein a method for making said selectivated transalkylation catalyst composition comprises:
   (i) contacting an untreated transalkylation catalyst composition with a selectivating solution to form said selectivated transalkylation catalyst, said transalkylation catalyst composition comprising a zeolite in acid form and having an MWW framework structure, said selectivating solution comprises water and a cation or an anion of an element in Group 1, Group 2, or Group 17 of the Periodic Table, wherein said selectivated transalkylation catalyst composition has a higher selectivity to ethylbenzene than the selectivity of said transalkylation catalyst composition that has not been contacted with said selectivating solution when the catalysts are compared under equivalent transalkylation conditions,
   wherein said element in Group 1 is sodium or potassium, said element in Group 2 is calcium, and said element in Group 17 is chlorine,
   wherein said selectivating solution comprises dissolved ions which include one or more of the following elements: calcium in an amount from 600 to 750 milligrams per liter (mg/L), sodium in an amount from 400 to 500 mg/L, potassium in an amount from 40 to 80 mg/L, and chlorine in an amount from 650 to 850 mg/L,
   wherein step (i) comprises contacting said untreated transalkylation catalyst composition with said selectivating solution for 1 hour or more at a temperature in a range of 20° C. to 95° C. and at a pH of the selectivating solution in a range of 6.5 to 8.0.

2. The process of claim 1, wherein said selectivated transalkylation catalyst composition produces a lower amount of xylene by-product of an ethylbenzene process than said transalkylation catalyst composition that has not been contacted with a selectivating solution when the catalysts are compared under equivalent transalkylation conditions.

3. The process of claim 1, further comprising:

(ii) drying said selectivated transalkylation catalyst composition with an inert gas for 1 hour or more at ambient pressure and at temperature of less than 300° C.

4. The process of claim 3, wherein said inert gas comprises nitrogen, oxygen, air or a mixture thereof.

5. The process of claim 1, further comprising:

(iii) contacting said selectivated transalkylation catalyst with benzene for 1 hour or more.

6. The process of claim 1, further comprising:

(d) separating said transalkylation effluent stream to recover an ethylbenzene stream.

7. The process of claim 1, wherein said at least partially liquid phase transalkylation conditions include a temperature of 150 to 260° C. and a pressure of 696 to 4137 kPa-a (101 to 600 psia).

8. The process of claim 7, further comprising:

(e) contacting a benzene stream with an alkylating agent stream under alkylation conditions and in presence of an alkylation catalyst to produce an alkylation effluent which comprises a mono-alkylated benzene and said poly-alkylated benzene.

9. The process of claim 8, further comprising:

(f) separating said alkylation effluent to recover a poly-alkylated benzene stream; and (g) supplying said poly-alkylated benzene stream to step (b).

10. The process of claim 8, wherein said alkylating agent stream comprises ethylene.

11. The process of claim 8, wherein said alkylation conditions are at least partially liquid phase conditions and include a temperature of 10° C. to 400° C. and a pressure of up to about 25000 kPa, and a WHSV based on weight of said alkylating agent from about 0.1 $hr^{-1}$ to about 100 $hr^{-1}$.

12. The process of claim 1, wherein said stream comprising benzene further comprises impurities, said stream comprising benzene is contacted with a guard bed material to remove at least a portion of said impurities, and said guard bed material comprises a large pore zeolite having a framework structure type selected from the group consisting of FAU, *BEA, MWW, MOR and mixtures thereof.

13. The process of claim 1, wherein said zeolite which has said MWW framework structure is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, UZM-37, MIT-1, ITQ-1, ITQ-2, ITQ-30 and mixtures of two or more thereof.

14. The process of claim 13, wherein said zeolite which has said MWW framework structure is MCM-22.

* * * * *